US012667299B2

(12) United States Patent
Bollinger et al.

(10) Patent No.: US 12,667,299 B2
(45) Date of Patent: Jun. 30, 2026

(54) METHODS AND APPARATUS FOR TRIGGERING A STIMULUS FOR EVOKED BRAIN RESPONSE ANALYSIS

(71) Applicant: Health Tech Connex Inc., Surrey (CA)

(72) Inventors: Fabio Bollinger, Langley (CA); Ryan Clarke Newell D'Arcy, North Vancouver (CA); Benjamin Davies, Surrey (CA); Shaun Dean Fickling, Coquitlam (CA); Zachary Frehlick, Vancouver (CA); Sandeep Gurm, Surrey (CA); Oliver Steiner, Surrey (CA)

(73) Assignee: Health Tech Connex Inc., Surrey (CA)

( * ) Notice: Subject to any disclaimer, the term of this patent is extended or adjusted under 35 U.S.C. 154(b) by 859 days.

(21) Appl. No.: 17/481,146

(22) Filed: Sep. 21, 2021

(65) Prior Publication Data

US 2022/0110578 A1     Apr. 14, 2022

Related U.S. Application Data

(60) Provisional application No. 63/081,814, filed on Sep. 22, 2020.

(51) Int. Cl.
*A61B 5/38* (2021.01)
*A61B 5/00* (2006.01)
(Continued)

(52) U.S. Cl.
CPC .................. *A61B 5/38* (2021.01); *A61B 5/31* (2021.01); *A61B 5/372* (2021.01); *A61B 5/7285* (2013.01)

(58) Field of Classification Search
CPC .. A61B 5/38; A61B 5/31; A61B 5/372; A61B 5/7285; A61B 5/384
See application file for complete search history.

(56) References Cited

U.S. PATENT DOCUMENTS

| | | | |
|---|---|---|---|
| 4,080,637 A | 3/1978 | Chase et al. | |
| 5,730,146 A | 3/1998 | Itil et al. | |

(Continued)

FOREIGN PATENT DOCUMENTS

WO     2016/004111 A1     1/2016

OTHER PUBLICATIONS

Charles E. Davis et al., Stimulus Onset Hub: an Open-Source, Low Latency, and Opto-Isolated Trigger Box for Neuroscientific Research Replicability and Beyond, Frontiers in Neuroinformatics, www.frontiersin.org, Feb. 6, 2020, 9 pages, vol. 14, Article 2, doi: 10.3389/fninf.2020.00002.

(Continued)

*Primary Examiner* — Tse W Chen
*Assistant Examiner* — Joseph A Tombers
(74) *Attorney, Agent, or Firm* — McCarthy Tétrault LLP; Amy Fong

(57) ABSTRACT

Methods and apparatus are described for synchronizing a stimulus with EEG data for research and clinical and consumer applications using EEG and ECG devices. An input/output adapter for stimulus timing includes an adapter input port for receiving an encoded audio file played from an audio output device. The audio file has a first channel carrying trigger data and a second channel carrying stimulus data. The adapter is configured to separate the encoded audio file into its first and second channels; read the trigger data in the first channel and generate a trigger signal for delivery to an EEG data logger; and read the stimulus data in the second channel and generate an auditory signal for delivery to an audio playback device. Timing errors in regard to stimulus onsets are addressed by the synchronized transmission of the trigger signal and auditory signal.

20 Claims, 4 Drawing Sheets

(51) Int. Cl.
    *A61B 5/31*         (2021.01)
    *A61B 5/372*     (2021.01)

(56)          References Cited

U.S. PATENT DOCUMENTS

| | | | |
|---|---|---|---|
| 6,071,229 A * | 6/2000 | Rubins ................. | A61M 21/00 |
| | | | 600/27 |
| 2003/0088161 A1 * | 5/2003 | Stengel ................. | A61B 5/002 |
| | | | 128/903 |
| 2006/0132382 A1 | 6/2006 | Jannard | |
| 2010/0076338 A1 * | 3/2010 | Kwak .................... | A61B 5/125 |
| | | | 600/559 |
| 2019/0104960 A1 * | 4/2019 | Abramov ............. | A61B 5/7282 |

OTHER PUBLICATIONS

N. Jeremy Hill et al., audiomath: A neuroscientist's sound toolkit, https://doi.org/10.1016/j.heliyon.2021.e06236, Feb. 10, 2021, 11 pages , vol. 7, Issue 2, E06236, Elsevier Ltd.

* cited by examiner

METHODS AND APPARATUS FOR TRIGGERING A STIMULUS FOR EVOKED BRAIN RESPONSE ANALYSIS

RELATED APPLICATIONS

This application claims priority from U.S. Patent Application No. 63/081,814 filed on Sep. 22, 2020 entitled "METHODS AND APPARATUS FOR TRIGGERING A STIMULUS FOR EVOKED BRAIN RESPONSE ANALYSIS". This application claims the benefit under 35 U.S.C. § 119 of U.S. Patent Application No. 63/081,814 filed on Sep. 22, 2020 entitled "METHODS AND APPARATUS FOR TRIGGERING A STIMULUS FOR EVOKED BRAIN RESPONSE ANALYSIS", which is incorporated herein by reference in its entirety for all purposes.

TECHNICAL FIELD

The present disclosure relates generally to methods and apparatus for triggering stimuli to evoke brain responses. Particular embodiments address timing (i.e., latency) issues in hardware triggering. Applications include research, and clinical and consumer uses of evoked brain responses measured by brain sensing technologies such as electroencephalography and magnetoencephalography.

BACKGROUND

The brain's response to a stimulus can be measured using technologies such as electroencephalography (EEG) and magnetoencephalography (MEG). EEG and MEG can be used to collect evoked responses such as event-related potentials (ERP) and evoked potentials (EP). The stimulus can be auditory, visual, somatosensory, and the like. In order to measure the evoked brain response, one needs to determine the time at which the stimuli are presented (stimulus onset). In the case of an auditory stimulus, the time at which audio playback is activated can provide an estimate of the stimuli onset time. Activation of playback can be determined, for example, by monitoring when bytes of a digital audio file are received at the sound card. In response to receiving the audio file, the sound card plays the audio file and outputs a signal to an audio jack in the patient's headset or other audio playback device. However, there is generally some delay between when the audio file is received by the sound card, and when the audio signal is delivered to the audio jack. Such latency varies according to the particular characteristics of the hardware (sound card) and operating system. For example, sound cards may be allocated memory by the operating system according to a certain priority, where the higher the priority, the lower the latency. In measuring evoked responses to auditory stimuli, the delay between receipt of the audio file and stimulus onset is generally within a range of between 10 ms to 30 ms. In order to provide meaningful evoked response data, the absolute latency can be measured and logged, therefore, eliminating inherent timing errors. Accurate latencies can then be accounted for in analyzing the brain's response to stimuli.

There is a need for improved brain sensing devices that can be used in collecting increasingly accurate data for evoked brain responses, which minimize the timing errors in regard to the onsets of stimuli. There is a need for improved apparatus and methods for the triggering of hardware that mitigate or avoid the latency issues noted above.

SUMMARY OF THE DISCLOSURE

In general, the present specification describes methods and apparatus for synchronizing a stimulus with EEG data for behavioural and medical research using EEG and ECG devices. An input/output adapter for stimulus timing includes an adapter input port for receiving an encoded audio file played from an audio output device. The encoded file has a first channel carrying trigger data and a second channel carrying stimulus data. The adapter is configured to separate the encoded audio file into its first and second channels; read the trigger data in the first channel and generate a trigger signal for delivery to an EEG data logger; and read the stimulus data in the second channel and generate an auditory signal for delivery to an audio playback device. Latency with respect to playback by an audio output device is addressed by providing an encoded audio file for playback to the input/output adapter, and the input/output adapter enabling the synchronized transmission of the trigger signal and auditory signal.

One aspect of the invention provides an input/output adapter for stimulus timing. The adapter includes an adapter input port for receiving an encoded audio file played from an audio output device, the audio file comprising a first channel carrying trigger data and a second channel carrying stimulus data. The adapter also includes a trigger generation circuit configured to read the trigger data in the first channel and generate a trigger signal, and a stimulus generation circuit configured to read the stimulus data in the second channel and generate an auditory signal. A trigger output port in the adapter receives the trigger signal and delivers the trigger signal to an EEG data logger. An audio output port in the adapter receives the auditory signal and delivers the auditory signal to an audio playback device. A port is provided in the adapter for receiving power from a power supply for powering the decoder circuitry. The adapter input port is configured to separate the encoded audio file into its first and second channels and relay the first channel to the trigger generation circuit and simultaneously relay the second channel to the stimulus generation circuit.

In particular embodiments, the trigger generation circuit of the adapter is configured to detect a trigger byte in the trigger data and amplify the corresponding voltage of the trigger signal to within a voltage range detectable by the EEG data logger. The trigger generation circuit may include a negative edge detector for detecting the trigger byte in the trigger data.

In particular embodiments, the stimulus generation circuit of the adapter is configured to recombine the stimulus data into a two-channel auditory signal including a left channel and a right channel, both of which carry the auditory signal. The stimulus generation circuit may be configured to electronically amplify the auditory signal and duplicate the stimulus data across the left and the right channels. In some embodiments, delivery of the trigger signal to the EEG data logger by the trigger generation circuit is synchronized with the delivery of the auditory signal to the audio playback device by the stimulus generation circuit.

Another aspect of the invention relates to apparatus for determining the onset of a stimulus of an evoked response. The apparatus includes a system controller for generating an encoded audio file, an audio output device for playing the encoded audio file, an input/output adapter for receiving the encoded audio file played by the audio output device and simultaneously generating an auditory signal and a trigger signal, and ERP/EP acquisition hardware. The ERP/EP acquisition hardware includes a headset connected for playback of the auditory signal, a plurality of EEG electrodes positioned on or near the patient's scalp, and an EEG data logger for receiving EEG data from the plurality of EEG electrodes and the trigger signal from the adapter.

A further aspect of the invention is directed to a method for stimulus timing. The method includes: receiving an encoded audio file played from an audio output device, the encoded audio file having a first channel carrying trigger data and a second channel carrying stimulus data; separating the encoded audio file into its first and second channels; based on the trigger data in the first channel, generating a trigger signal; based on the stimulus data in the second channel, generating an auditory signal; delivering the trigger signal to an EEG data logger; and delivering the auditory signal to an audio playback device. Delivery of the trigger signal to the EEG data logger is synchronized with the delivery of the auditory signal to the audio playback device.

In particular embodiments, the method includes detecting a trigger byte in the trigger data and amplifying the corresponding voltage of the trigger signal to within a voltage range detectable by the EEG data logger. A negative edge detector may be used for detecting the trigger byte in the trigger data.

In particular embodiments, the method includes recombining the stimulus data into a two-channel auditory signal including a left channel and a right channel, both of which carry the auditory signal. The auditory signal may be electronically amplified. Recombining the stimulus data into a two-channel auditory signal may incorporate duplication of the stimulus data across the left and the right channels.

Another aspect provides a method for stimulus timing. The method includes receiving an encoded file, the encoded file comprising trigger data and stimulus data; decoding trigger data and stimulus data from the encoded file; based on the decoded trigger data, generating a trigger signal; based on the decoded stimulus data, generating a stimulus signal; delivering the trigger signal to a data logger; and delivering the stimulus signal to a stimulus generator; wherein delivery of the trigger signal to the data logger is synchronized with the delivery of the stimulus signal to the stimulus generator. In particular embodiments, decoding the encoded file includes separating the encoded file into a first channel carrying the trigger data and a second channel carrying the stimulus data. In embodiments where the stimulus data is for an auditory stimulus, the stimulus data is recombined into a two-channel auditory signal for delivery to the stimulus generator. Recombining of the stimulus data may include duplicating the stimulus data across the two channels of the auditory signal.

In other embodiments, the trigger data and the stimulus data are encoded on one channel and decoding the encoded file includes separating the trigger data and stimulus data from the channel.

In certain embodiments, trigger data and the stimulus data are each encoded on a corresponding channel of a plurality of channels and decoding the encoded file comprises separating the trigger data and the stimulus data from the plurality of channels. In some embodiments, decoding the encoded file includes separating the encoded file into a plurality of types of stimulus and a plurality of corresponding triggers.

Additional aspects of the present invention will be apparent in view of the description that follows.

BRIEF DESCRIPTION OF THE DRAWINGS

Features and advantages of the embodiments of the present invention will become apparent from the following detailed description, taken with reference to the appended drawings in which.

DETAILED DESCRIPTION

The description which follows, and the embodiments described therein, are provided by way of illustration of examples of particular embodiments of the principles of the present invention. These examples are provided for the purposes of explanation, and not limitation, of those principles and of the invention.

Described herein is an Evoked Potential Input Output (EPIO) adapter that enables EEG and MEG devices to collect evoked responses such as event-related potentials (ERP) and evoked potentials (EP) which are in response to delivered stimuli. The particular implementations described herein use auditory stimuli presented to the patient. Other types of stimuli (such as visual, somatosensory, mechanical, tactile, electrical, etc.) can be used for other implementations. The EPIO adapter provides stimuli time lock capabilities with a high degree of precision (in one particular implementation, within the sampling rate error of the EEG amplifier) while still delivering high fidelity auditory stimuli to the patient. The adapter permits hardware integration across a range of different EEG and MEG sensor configurations, spanning from high-density arrays to low density distant sensors for non-invasive measurement of evoked brain responses. Applications include research (such as behavioural and clinical research), and clinical and consumer uses of evoked brain responses measured by brain sensing technologies such as electroencephalography and magnetoencephalography, with the technical application theoretically adapted for any brain sensing technology that involves triggered stimulation (e.g., functional magnetic resonance imaging). While specific embodiments described herein are for evoked brain responses, the technologies described herein may be adapted for use for the measurement of non-brain physiological responses from various stimuli.

Figure 1:
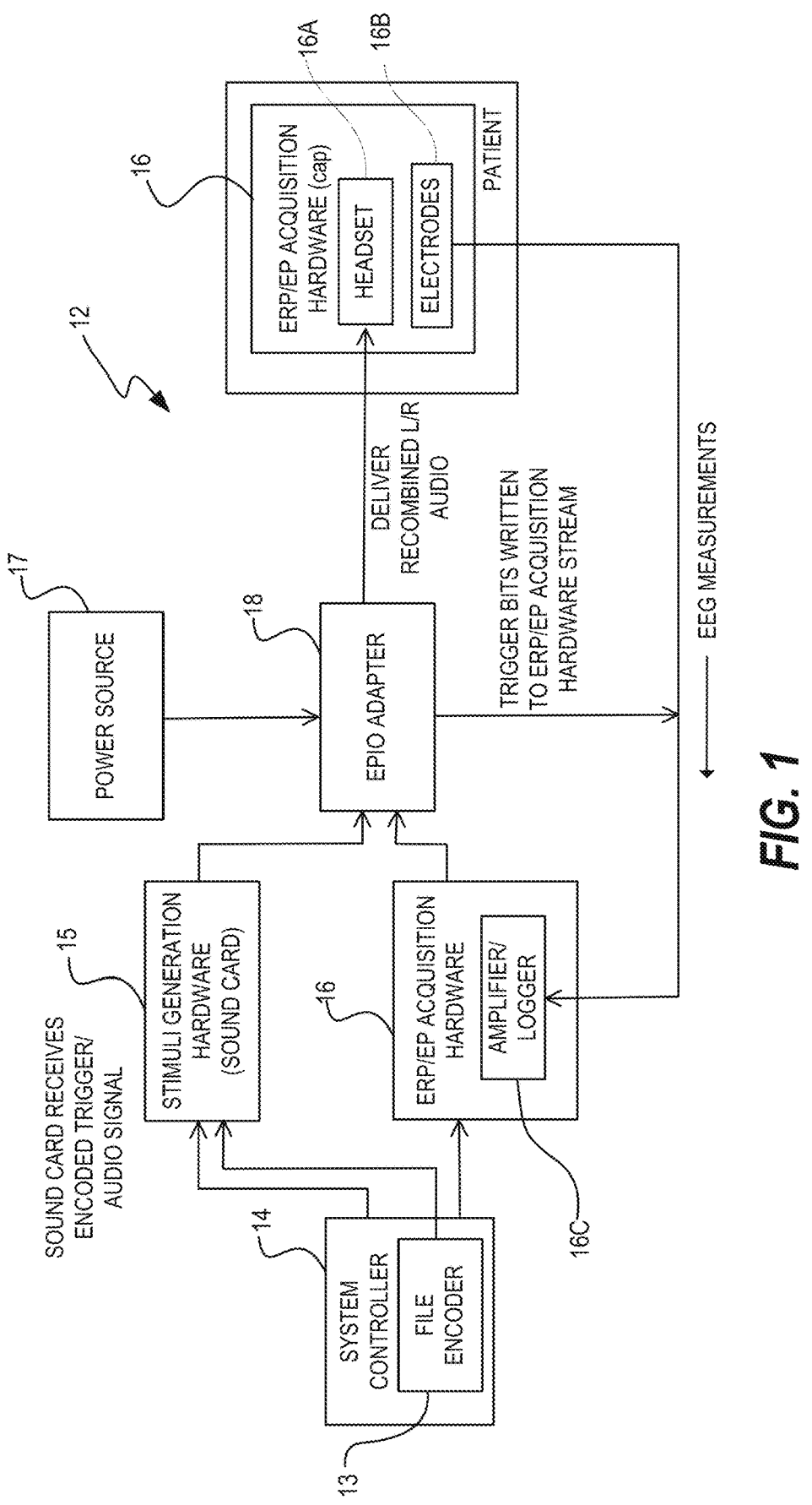
FIG. 1 shows a system for acquiring ERP/EP data, incorporating an evoked potential input/output adapter according to a particular embodiment.

FIG. 1 shows a system 12 for acquiring ERP/EP data, incorporating an EPIO adapter 18 according to a particular embodiment. System 12 includes a system controller 14 for providing an audio file, and a power source 17 for supplying power to EPIO adapter 18. System 12 further includes hardware for generating stimuli 15 and ERP/EP acquisition hardware 16, both of which receive output signals from EPIO adapter 18. Where the stimuli are auditory stimuli, stimuli generation hardware 15 may comprise an audio output device, such as a sound card, for playback of audio files received from system controller 14, and ERP/EP acquisition hardware 16 may comprise a headset 16A or some other audio playback device which converts an audio signal to sound. ERP/EP acquisition hardware 16 includes electrodes 16B positioned on or near the patient's scalp, and an amplifier and logger 16C that receives the ERP/EP responses from the brain as detected through the electrodes 16B. In some embodiments, the audio playback device, electrodes and/or amplifier/logger may reside within the same headset/cap apparatus that is worn by a patient, although this is not necessary, and in other cases, one or more of these components may be provided in separate devices.

The audio file delivered by system controller 14 may comprise a digital audio file encoded with stimulus data and trigger data, as described in more detail herein. Stimuli generation hardware 15 receives the encoded stimulus/trigger audio file from system controller 14, and outputs the file (via playback by the audio output device) to the EPIO adapter 18. Once the audio file is received by the EPIO adapter 18, the adapter 18 reads the audio file and simultaneously delivers the stimulus data to headset 16A (which plays the audio signal to the patient) and the trigger data to amplifier/logger 16C. The trigger data therefore becomes part of the data that is logged by amplifier/logger 16C (along with the ERP/EP response data) and indicates the onset of an auditory stimulus that evokes the response.

Particular embodiments of the invention re-purpose the multiple channels of audio files to facilitate delivery of simultaneous signals to the headset 16A and amplifier/logger 16C of ERP/EP acquisition hardware 16. In particular, embodiments of the invention utilize a two-channel encoded audio file to provide accurate triggering of auditory stimuli. A two-channel audio file is characterized by a "left" channel and "right" channel, which are conventionally used to deliver different audio signals to a "left" speaker and "right" speaker, respectively. This can be used to provide stereophonic sound. For example, a WAV audio format file may contain two-channel audio file sampled at a frequency of 44,100 Hz with an audio bit depth of 16 bits per sample. However, in accordance with embodiments of the invention, rather than using both channels in the audio file to deliver sound in a standard two-channel encoded audio file to the audio output device (stimuli generation hardware 15), a new two-channel audio file is encoded wherein only one of the channels is used to deliver the audio data samples, and the other of the channels is used to deliver trigger data. In the FIG. 1 embodiment, system controller 14 comprises an audio file encoder 13 that encodes the two-channel stimulus/trigger audio file for delivery to stimuli generation hardware 15 (which then plays it to EPIO adapter 18).

Figure 2:
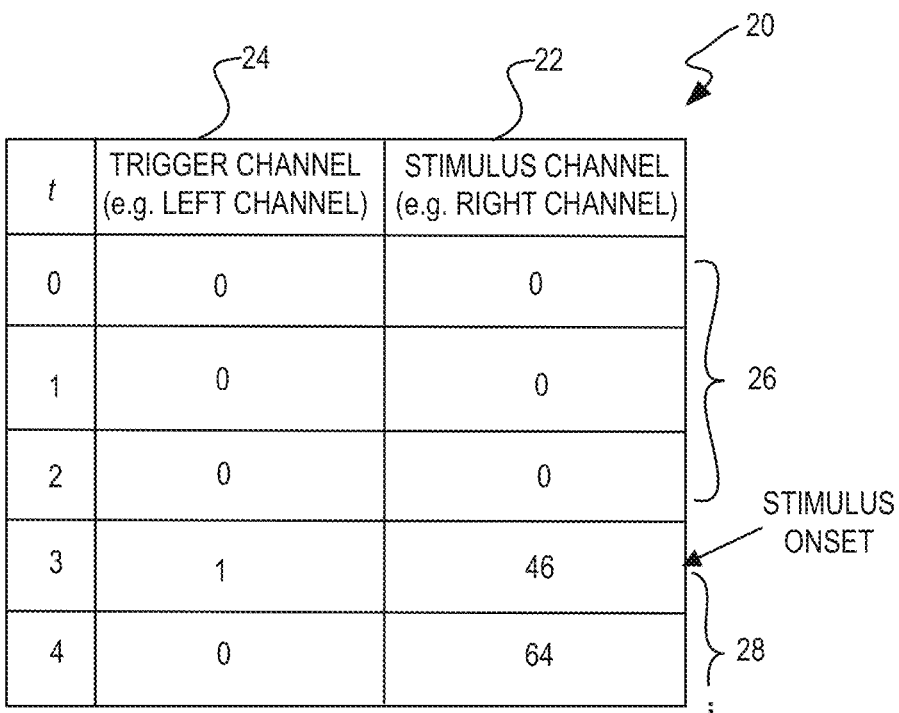
FIG. 2 shows a tabular representation of a sample data stream for a two-channel audio file encoded in accordance with a particular embodiment.

As seen in FIG. 2, a sample data stream of a two-channel audio file 20 encoded in this manner includes a first channel 22 (consisting of the right channel in the FIG. 2 example) comprising the stimulus data. First channel 22 is also referred to herein as the stimulus channel. The stimulus data is a stream of bytes of digital audio data samples (e.g. consisting of the transmission of 0, 0, 0, 46, 64 in the illustrated example). These audio data samples are eventually converted to sound by headset 16A for playback to the patient. Non-zero data samples at rows t=3, t=4 transmit an auditory stimuli 28 whereas the transmission of '0' as the value of a data sample (at rows t=0, t=1, and t=2) indicates no sound is played (i.e. a period of silence 26).

The two-channel audio file also includes a second channel 24 (consisting of the left channel in the FIG. 2 example) for the trigger signal (e.g. consisting of the transmission of 0, 0, 0, 1, 0 as the stream of trigger data). Second channel 24 is also referred to herein as the trigger channel. In the illustrated embodiment, the trigger signal is encoded as a sequence of binary numbers (0's and 1's), wherein 1 marks the occurrence of a trigger (at row t=3) corresponding to the onset of auditory stimuli 28 (aligning with the first appearance of a non-zero data sample after a sequence of 0's in the right channel), and 0 indicates otherwise (at rows t=0, t=1, t=2, and t=4 in FIG. 2). In other embodiments, the function and contents of the left and right channels are reversed (e.g. the right channel is for the trigger data and the left channel is for the stimulus data). As explained in further detail below, the two-channel encoded audio file in combination with the adapter circuitry ensures that simultaneous reading/writing of the stimulus data will be time synchronized with the trigger data. Although only five rows of data samples (from t=0 to t=5) are depicted in FIG. 2 for the purpose of explaining the encoding of a two-channel audio file according to an embodiment of the invention, it is to be understood that audio files that are used to generate auditory stimuli typically consist of a significantly larger number of data samples, and may include a longer string of 0's preceding the stimuli onset in the stimulus channel.

Figure 3:
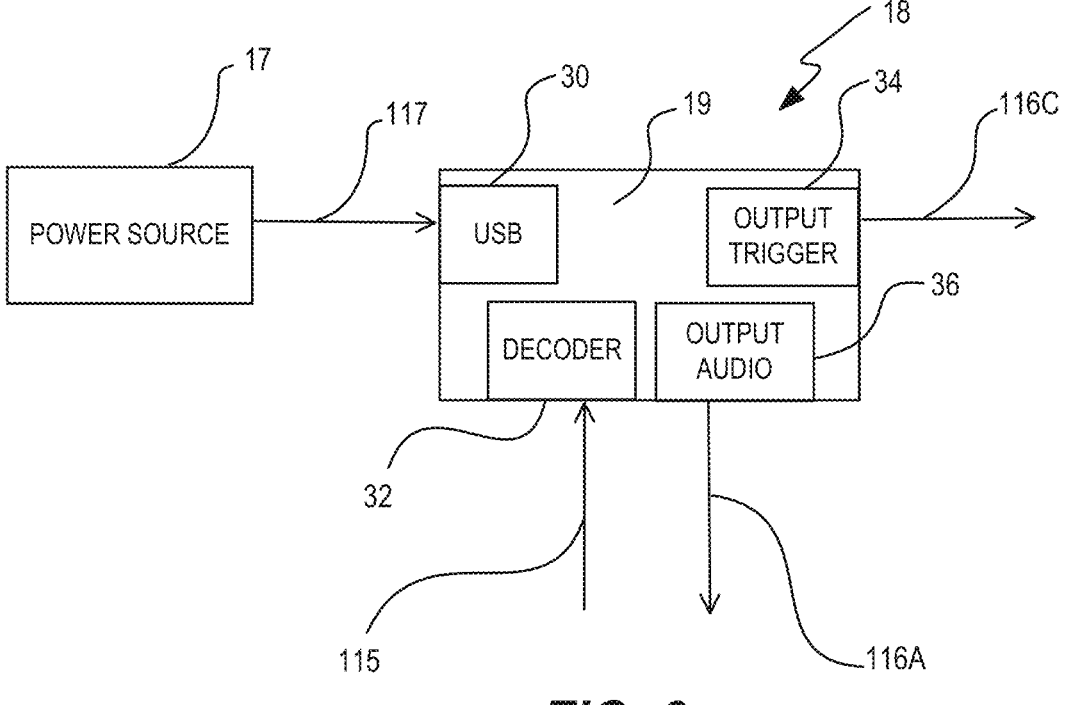
FIG. 3 shows an evoked potential input/output adapter that may be used in the FIG. 1 system according to a particular embodiment.

FIG. 3 is a schematic illustration of an EPIO adapter 18 according to one embodiment that may be used in the system 12 of FIG. 1 to accept a two-channel encoded audio file 20 having a stimulus channel 22 and a trigger channel 24 as described with reference to FIG. 2. Various input/output components of the EPIO adapter 18 are provided on a printed circuit board (PCB) 19, including: a Universal Serial Bus (USB) port 117 for receiving power from a USB power source 17, a decoder 32 for receiving via line-in 115 the encoded audio file 20 (as played out by stimuli generation hardware 15), output audio 36 with a line-out 116A for delivering the stimulus signal to the headset 16A of the ERP/EP acquisition hardware for playback to the patient, and output trigger 34 with a line out 116C for delivering the trigger signal to the amplifier/logger 16C of the ERP/EP acquisition hardware 16. Decoder 32 decodes the encoded audio file 20 received from the audio output device, to produce the stimuli and trigger signal that are output simultaneously via line-out 116A, 116C, respectively. Given that the delay associated with audio output device playback of the audio file has already occurred by the time the encoded audio file is received at the input to decoder 32, the output of the trigger and stimulus signal can be synchronized at EPIO adapter 18, eliminating or minimizing the latency between playback of the auditory stimulus at the headset and the trigger signal. Since the trigger signal is pushed (simultaneously with the onset/playback of the auditory stimuli) onto the same ERP/EP acquisition hardware stream that carries the EEG data (see FIG. 1), the read/write of the evoked response data is synchronized with the trigger data.

Figure 4:
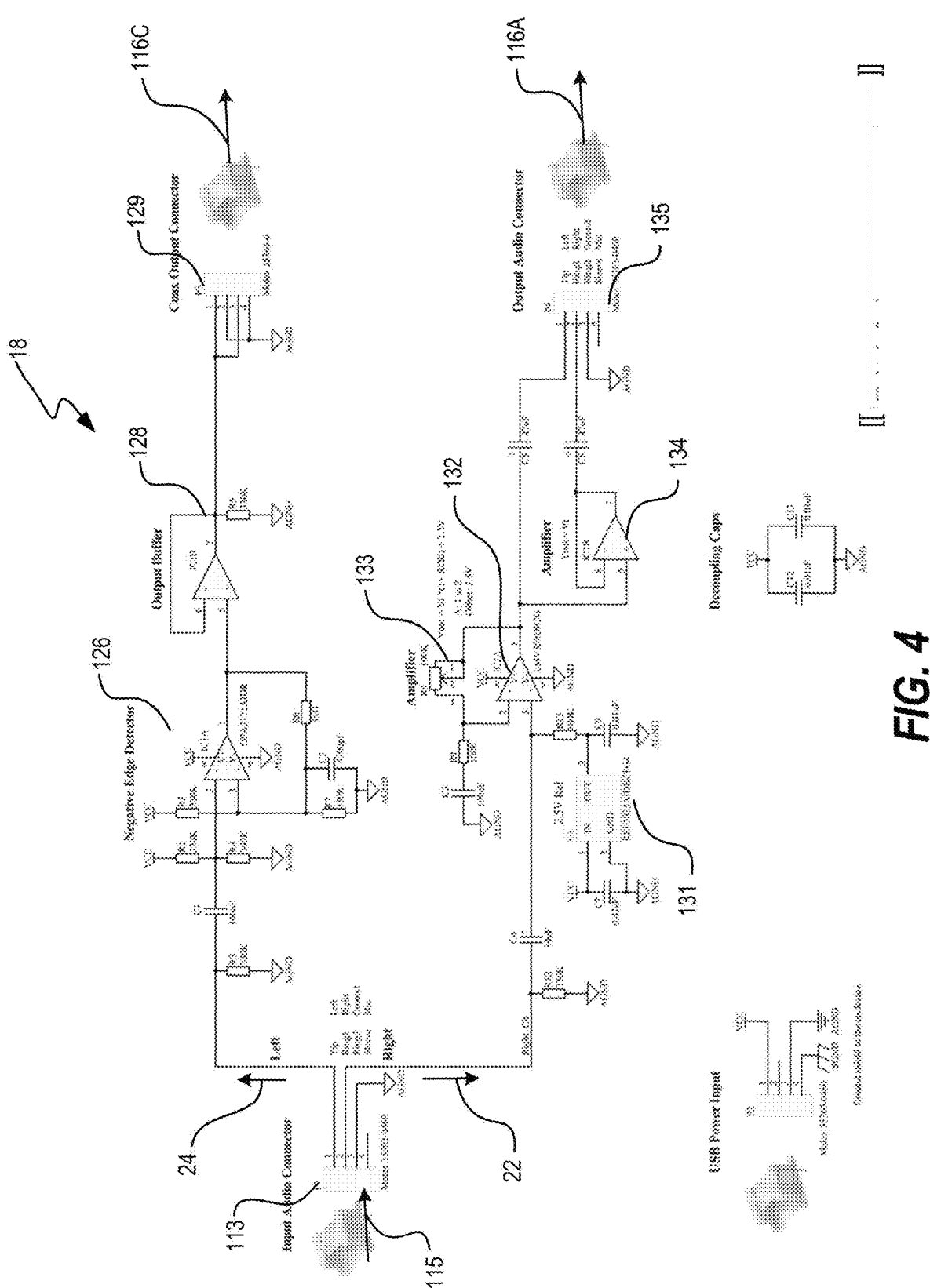
FIG. 4 shows a circuit diagram for the evoked potential input/output adapter of FIG. 3.

The operation of EPIO adapter 18 in decoding the encoded audio file 20 to produce the synchronized trigger and stimulus signal is explained in more detail with reference to the various circuitry components of EPIO adapter 18 illustrated in FIG. 4. As shown in FIG. 4, adapter 18 comprises circuitry (which provides the functionality of decoder 32 of FIG. 3) for reading and processing the two-channel audio file 20 and generating a stimulus signal based on data in the right channel 22 and a trigger signal based on data in the left channel 24 (or vice versa) and simultaneously delivering the stimulus signal and the trigger signal to the headset 16A and the amplifier/logger 16C, respectively. The EPIO adapter 18 comprises an input audio connector 113 which receives the audio file 20 on line-in 115, and transmits the left channel 24 to the trigger portion of the circuitry and the right channel 22 to the stimulus portion of the circuitry.

The trigger portion processes the left channel of the audio file 20 to produce a trigger signal that is conditioned to feed into any device that receives and monitors EEG data, such as EEG amplifiers, wireless earbuds, portable EEG headsets, and the like. As seen in FIG. 4, the trigger portion integrated circuit includes a negative edge detector 126. Negative edge detector 126 is configured to detect a "1" byte, after a series of "0"s in the file. The "1" byte is read by the negative edge detector 126 as a "high" voltage. The "1" indicates the trigger (corresponding to the start or onset of the stimulus in the right channel). Since the signal provided by the "1" byte may not be of sufficiently high voltage to be detected by the amplifier/logger of the ERP/EP acquisition hardware, the integrated circuit incorporates an amplifier (at output buffer 128) for conditioning the negative edge detected signal to within a voltage range that is detectable by the amplifier/logger.

The stimulus portion processes the right channel of the audio file 20, by duplicating (at channel duplicator 133 of FIG. 4) the right channel into a second audio channel. The result is a recombined two-channel audio file 20 provided to output audio connector 135, wherein the auditory stimulus is duplicated across both channels. The two-channel audio file is sent via line out 116 to the audio jack in the headset. Losses may result from splitting of the channel into two channels, at the connectors and circuit traces. Such losses can be counteracted by amplification, including for example, by way of electronic amplifiers 131, 132 and 134 of FIG. 4.

Figure 5:
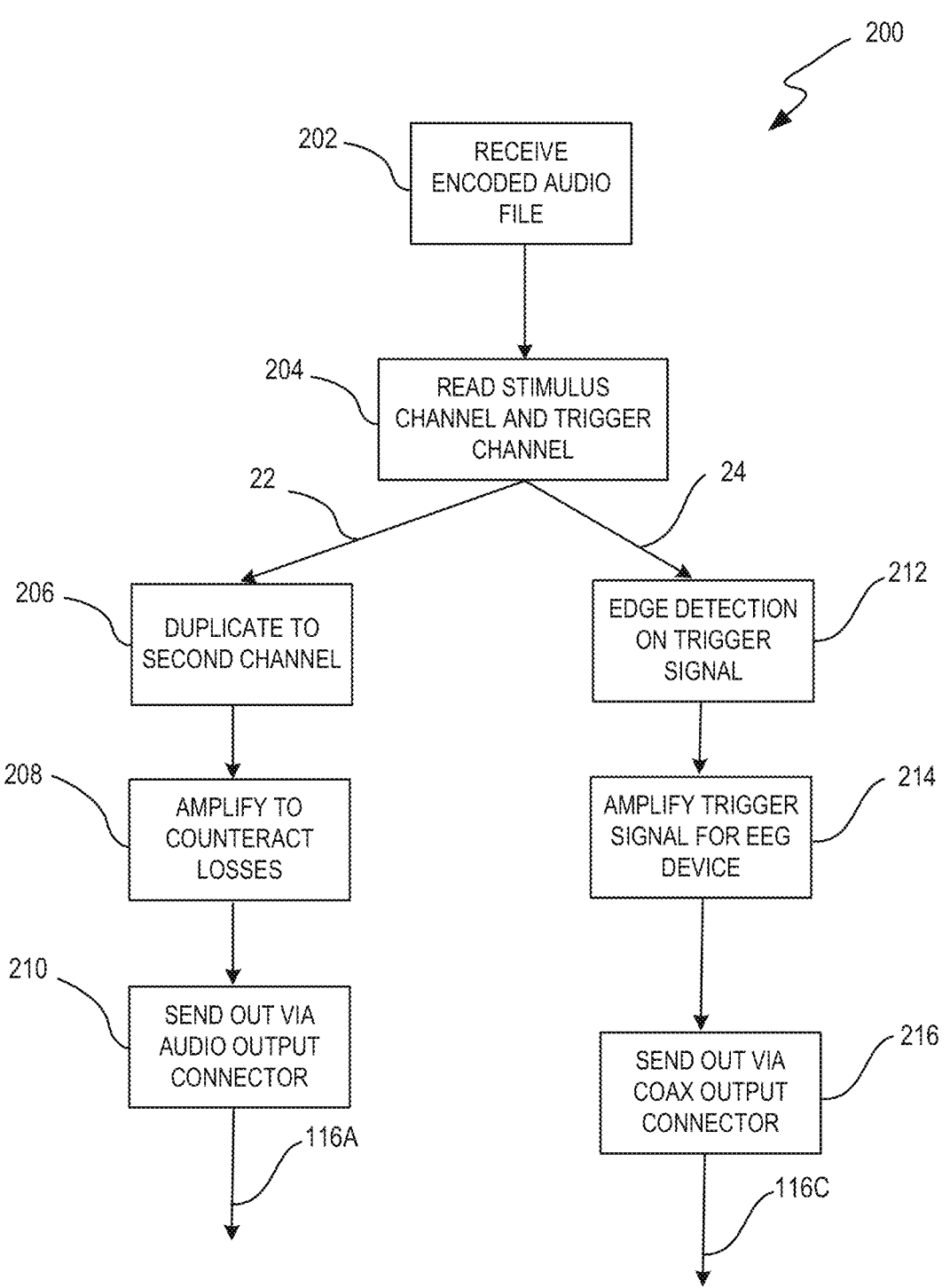
FIG. 5 is a flowchart of a method executed by the evoked potential input/output adapter of FIG. 3 according to one embodiment.

FIG. 5 is a flowchart of a method 200 that may be implemented by EPIO adapter 18 to achieve synchronized playback of the auditory stimulus at the headset with a trigger signal, using the encoded audio file described herein. Method 200 begins by receiving at block 202 the two-channel encoded audio file (which contains stimulus data in one channel and trigger data in the other channel). The two channels are read at block 204 and sent to separate portions of the circuit. For channel 22 containing the stimulus data, the stimulus data is duplicated at block 206 to a second channel, and the signal is amplified at block 208 (to counteract against losses of the type as noted above). The recombined two-channel audio file (containing the auditory stimulus to be played at the headset) is then set out via the audio output connector at block 210 (via line-out 116A). Simultaneously with the processing of the stimulus channel 22, channel 24 containing the trigger data is sent to an edge detection circuit at block 212, to detect the presence of a trigger signal. The trigger signal is amplified at block 214, so as to be capable of being read by the amplifier/logger of the ERP/EP acquisition hardware. The trigger signal is then sent via coax output connector at block 216 to line-out 116C, for transmission to the logger of the ERP/EP acquisition hardware. This enables the trigger signal to be logged along with the EEG measurements that are detected by the electrodes in the patient's cap (which are also sent to the logger of the ERP/EP acquisition hardware). The trigger signal indicates the onset of the auditory stimulus that evokes the response.

The applications of the EPIO adapter 18 described herein include any application where it is important to be able to determine the onset of a particular stimulus that evoked a response being measured in the patient's brain. These include behavioural and medical research applications, and clinical and consumer uses of evoked brain responses measured by brain sensing technologies such as electroencephalography and magnetoencephalography, with the technical application theoretically adapted for any brain sensing technology that involves triggered stimulation (e.g., functional magnetic resonance imaging). Addressing timing errors (e.g. latency) in the onsets of stimuli is important for emerging technologies that integrate brain sensing hardware with advances in existing stimulation devices, such as portable ear-bud-type earphones which can be used to detect evoked brain responses (in addition to playback of auditory stimuli). However, embodiments of the invention can be applied toward other applications where it is important to synchronize a trigger with an output. These applications may include measuring non-brain physiological responses (e.g. electromyography (EMG)), measuring evoked responses in the brain or other types of responses to other kinds of stimuli (e.g. visual, somatosensory, mechanical, tactile, electrical, etc.), and special effects (e.g. synchronizing audio output with a pyrotechnic event, by encoding the audio file with trigger events, and connecting the output of the input/output adapter to the pyrotechnic trigger.)

While according to particular embodiments the encoding of stimuli and trigger is directed to detection of the stimulus onset, in other embodiments some other feature of stimulus timing may be identified, such as stimulus offset or a milestone in continuous stimulus. For example, in a spoken text, triggers may indicate each word in the text or each syllable. In a pattern of auditory tones, a trigger may indicate either a tone or an interruption of the pattern, such as no sound where a sound is expected.

The embodiment described herein in relation to FIGS. 2 to 4 has one stimulus and one trigger encoded into an audio file and decoded by the EPIO. However, other embodiments for detecting stimulus onsets or other stimulus timing features may incorporate a plurality of types of stimuli and a plurality of corresponding triggers that are encoded together. For example, an auditory stimulus and an electrical stimulus may be encoded together, with corresponding trigger signals for each stimulus type. In this way, the same circuit would both synchronize and coordinate multiple stimuli and provide their precise timing. Applications for this may include multi-modal stimulus patterns, where a patient attends to different types of inputs, such as sound and images, either simultaneously or as part of a coordinated pattern, to maximize the brain functions measured during one assessment.

While the embodiment described herein in relation to FIGS. 2 to 4 makes use of audio ports (for which two output channels may be used for the stimulus and trigger), in alternate embodiments an EPIO adapter may be provided with more than two output channels, or one channel that encodes stimulus and triggers together. The methods described herein may be adapted for encoding these various stimuli and triggers together (to ensure precision in timing after decoding); the information can then be synchronously decoded for sending to its endpoint (e.g. headphones, electrical stimulator, LED display, etc.). For example, where one audio channel encodes both audio stimulus and trigger stimulus, the EPIO adapter may detect and remove the trigger from the audio, so that the trigger is recovered and the audio is not distorted. In this way, two audio channels could carry two different audio stimuli, with corresponding triggers, presenting a different stimulus to each of a patient's ears. Similarly, the EPIO adapter may monitor the stimulus itself to infer the location of triggers, such as where a sound begins after a period of silence, and generate a trigger for that stimulus.

In some embodiments, the encoded connection is bidirectional, with information going back to the controller from the EPIO adapter. For example, a circuit can be added to detect headphone connection by passing the stimulus back to the microphone channel. Alternatively, the circuit may return feedback from the patient, such as by the patient pressing a button or flipping a switch, so that the controller can dynamically modify the stimulus according to patient behavior.

The implementation of the EPIO adapter functions described with reference to FIGS. 1 to 4 may be provided, in other embodiments, through another circuit or components (e.g. a sound card or EEG amplifier that provides the EPIO functions described herein). In certain embodiments, various components may be incorporated to increase electrical safety and resistance to electrostatic shock. In this way, the EPIO may be either a discrete component or a part of a more complex component with multiple features and functions.

Particular embodiments of the invention can be modified to include wireless transmission of signals between certain components. For example, the trigger data and/or EEG data that are written to the ERP/EP acquisition hardware data stream may be sent over a wireless connection to the amplifier/logger 16C of the ERP/EP acquisition hardware 16. The recombined left/right audio file that is generated by the EPIO adapter 18 may be delivered over a wireless connection to the headset 16A worn by the patient.

The examples and corresponding diagrams used herein are for illustrative purposes only. Different configurations and terminology can be used without departing from the principles expressed herein.

Although the invention has been described with reference to certain specific embodiments, various modifications thereof will be apparent to those skilled in the art without departing from the scope of the invention. The scope of the claims should not be limited by the illustrative embodiments set forth in the examples, but should be given the broadest interpretation consistent with the description as a whole.

The invention claimed is:

1. An input/output adapter for stimulus timing, comprising:
   (a) an adapter input port for receiving as input an encoded audio file played from an audio output device, the encoded audio file comprising a first channel carrying trigger data and a second channel carrying stimulus data;
   (b) a trigger generation circuit configured to read from the encoded audio file the trigger data in the first channel and generate an output trigger signal;
   (c) a stimulus generation circuit configured to read from the encoded audio file the stimulus data in the second channel and generate an output auditory signal;
   (d) a trigger output port for receiving the output trigger signal and delivering as output the output trigger signal to an EEG data logger;
   (e) an audio output port for receiving the output auditory signal and delivering as output the output auditory signal to an audio playback device; and
   (f) a port for receiving power from a power supply for powering the input/output adapter circuitry;
      wherein the first channel carrying the trigger data is synchronized with the second channel carrying the stimulus data;
      wherein the adapter input port is configured to separate the encoded audio file into the first channel and the second channel and relay the first channel to the trigger generation circuit and simultaneously relay the second channel to the stimulus generation circuit,
      wherein the trigger generation circuit is configured to generate the output trigger signal without reading the stimulus data in the second channel, and
      wherein the stimulus generation circuit is configured to generate the output auditory signal without reading the trigger data in the first channel.

2. The input/output adapter of claim 1, wherein the trigger generation circuit is configured to detect a trigger byte in the trigger data and amplify the corresponding voltage output of the trigger signal to within a voltage range detectable by the EEG data logger.

3. The input/output adapter of claim 2, wherein the trigger generation circuit comprises a negative edge detector for detecting the trigger byte in the trigger data.

4. The input/output adapter of claim 1, wherein the stimulus generation circuit is configured to recombine the stimulus data into a two-channel output auditory signal comprising a left channel and a right channel, both the left channel and the right channel carrying the output auditory signal.

5. The input/output adapter of claim 4, wherein the stimulus generation circuit is configured to electronically amplify the output auditory signal.

6. The input/output adapter of claim 5, wherein the stimulus generation circuit is configured to duplicate the stimulus data across the left channel and the right channel.

7. The input/output adapter of claim 1, wherein delivery of the output trigger signal to the EEG data logger by the trigger generation circuit of the input/output adapter is synchronized with the delivery of the output auditory signal to the audio playback device by the stimulus generation circuit of the input/output adapter.

8. An apparatus for stimulus timing of an evoked response, comprising:
   (a) a system controller for generating an encoded audio file;
   (b) an audio output device for receiving and playing the encoded audio file;
   (c) an input/output adapter for receiving the encoded audio file played by the audio output device and simultaneously generating an output auditory signal and an output trigger signal, the input/output adapter comprising:
      an adapter input port for receiving as input the encoded audio file played by the audio output device, the encoded audio file comprising a first channel carrying trigger data and a second channel carrying stimulus data;
      a trigger generation circuit configured to read from the encoded audio file the trigger data in the first channel and generate the output trigger signal;
      a stimulus generation circuit configured to read from the encoded audio file the stimulus data in the second channel and generate the output auditory signal;
      a trigger output port for receiving the output trigger signal and delivering as output the output trigger signal to an EEG data logger;
      an audio output port for receiving the output auditory signal and delivering as output the output auditory signal to an audio playback device; and
      a port for receiving power from a power supply for powering the input/output adapter circuitry;
      wherein the first channel carrying the trigger data is synchronized with the second channel carrying the stimulus data;
      wherein the adapter input port is configured to separate the encoded audio file into the first channel and the second channel and relay the first channel to the trigger generation circuit and simultaneously relay the second channel to the stimulus generation circuit,
      wherein the trigger generation circuit is configured to generate the output trigger signal without reading the stimulus data from the second channel, and wherein the stimulus generation circuit is configured to generate the output auditory signal without reading the trigger data from the first channel; and (d) ERP/EP acquisition hardware, comprising a headset connected for playback of the auditory signal, a plurality of EEG electrodes, and the EEG data logger for receiving EEG data from the plurality of EEG electrodes and the trigger signal from the input/output adapter.

9. A method for stimulus timing, comprising:

(a) receiving as input an encoded audio file played from an audio output device to a decoder, the encoded audio file comprising a first channel carrying trigger data and a second channel carrying stimulus data;

(b) decoding the encoded audio file into the first channel and the second channel;

(c) based on the trigger data in the first channel and without reading the stimulus data in the second channel, generating an output trigger signal;

(d) based on the stimulus data in the second channel and without reading the trigger data from the first channel, generating an output auditory signal;

(e) delivering as output the output trigger signal to an EEG data logger; and (f) delivering as output the output auditory signal to an audio playback device;

wherein the first channel carrying the trigger data is synchronized with the second channel carrying the stimulus data;

wherein delivery of the output trigger signal to the EEG data logger is synchronized with the delivery of the output auditory signal to the audio playback device.

10. The method of claim 9, comprising detecting a trigger byte in the trigger data and amplifying the corresponding voltage of the output trigger signal to within a voltage range detectable by the EEG data logger.

11. The method of claim 10, comprising providing a negative edge detector for detecting the trigger byte in the trigger data.

12. The method of claim 9, comprising recombining the stimulus data into a two-channel output auditory signal comprising a left channel and a right channel, both the left channel and the right channel carrying the output auditory signal.

13. The method of claim 12, comprising electronically amplifying the output auditory signal.

14. The method of claim 13, wherein recombining the stimulus data into a two-channel output auditory signal comprises duplicating the stimulus data across the left channel and the right channel.

15. A method for stimulus timing, comprising:

(a) receiving as input an encoded file, the encoded file comprising trigger data and stimulus data;

(b) decoding the trigger data and the stimulus data from the encoded file;

(c) based on the decoded trigger data and without reading the decoded stimulus data, generating an output trigger signal;

(d) based on the decoded stimulus data and without reading the decoded trigger data, generating an output stimulus signal;

(e) delivering as output the output trigger signal to a data logger; and (f) delivering as output the output stimulus signal to a stimulus generator;

wherein the trigger data is synchronized with the stimulus data;

wherein delivery of the output trigger signal to the data logger is synchronized with the delivery of the output stimulus signal to the stimulus generator.

16. The method of claim 15, wherein decoding the encoded file comprises separating the encoded file into a first channel carrying the trigger data and a second channel carrying the stimulus data.

17. The method of claim 16, wherein the stimulus data is for an auditory stimulus, and the method comprises recombining the stimulus data into a two-channel auditory signal for delivery to the stimulus generator by duplicating the stimulus data across both channels of the two-channel auditory signal.

18. The method of claim 15, wherein the trigger data and the stimulus data are encoded on one input channel and decoding the encoded file comprises separating the trigger data and stimulus data from the one input channel.

19. The method of claim 15, wherein the trigger data and the stimulus data are each encoded on a corresponding channel of a plurality of channels and decoding the encoded file comprises separating the trigger data and the stimulus data from the plurality of channels.

20. The method of claim 15, wherein decoding the encoded file comprises separating the encoded file into a plurality of types of stimulus and a plurality of corresponding triggers.

* * * * *